United States Patent [19]

Ibe et al.

[11] 4,366,438
[45] Dec. 28, 1982

[54] SODIUM IONIZATION DETECTOR

[75] Inventors: Hidefumi Ibe, Hitachi; Izumi Yamada, Tokai, both of Japan

[73] Assignee: Hitachi, Ltd., Tokyo, Japan

[21] Appl. No.: 83,658

[22] Filed: Oct. 11, 1979

[30] Foreign Application Priority Data

Oct. 11, 1978 [JP] Japan ............................. 53-124172
Nov. 8, 1978 [JP] Japan ............................. 53-136743

[51] Int. Cl.³ .......................................... G01N 27/00
[52] U.S. Cl. .................................... 324/468; 324/466
[58] Field of Search ............... 324/464, 465, 466, 467, 324/468, 469, 470, 132; 73/26

[56] References Cited

U.S. PATENT DOCUMENTS 2,934,694  4/1960  Vacca ................................. 324/468
3,739,260  6/1973  Schadler ............................. 324/468
4,117,396  9/1978  Berkey et al. ....................... 324/468

*Primary Examiner*—Ernest F. Karlsen
*Attorney, Agent, or Firm*—Antonelli, Terry & Wands

[57] ABSTRACT

Disclosed is a sodium ionization detector (SID) for detecting sodium leaks by detecting the magnitude of fluctuation of the ion current produced by thermally ionizing sodium. There is a particular relationship between the magnitude of fluctuation of the ion current and the concentration of sodium. The sodium ionization detector is adapted to determine the magnitude of fluctuation of the ion current so as to compare it with a predetermined value. The magnitude of fluctuation of the ion current is determined, for example, by the root-mean-square value of a fluctuation component of the ion current.

3 Claims, 12 Drawing Figures

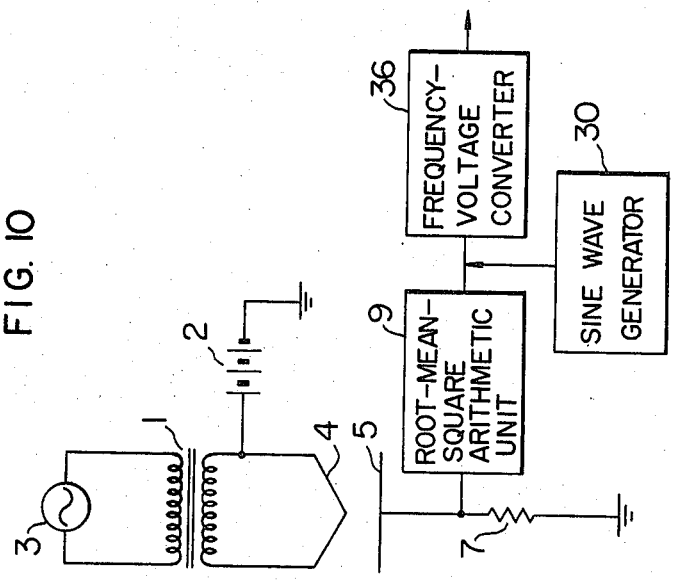
FIG. 10
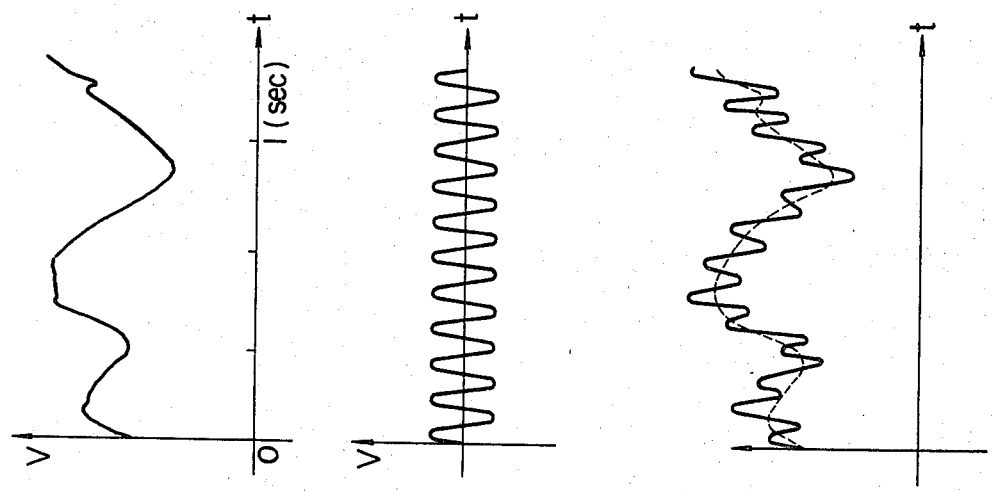
FIG. 8a
FIG. 8b
FIG. 8c

SODIUM IONIZATION DETECTOR

BACKGROUND OF THE INVENTION

This invention relates to a sodium ionization detector for detecting leaks of liquid sodium as a coolant for fast breeder nuclear reactors.

The conventional sodium ionization detector (hereinafter abbreviated to SID) comprises a transformer, an A.C. high power supply connected to the primary winding of the transformer, a filament connected to the secondary winding of the transformer, a collector located in facing relation with the filament so as to collect ionized sodium, a D.C. power supply for applying D.C. voltage between the collector and the filament, and an ammeter connected to the collector so as to measure ion current.

The sodium leaking from a sodium carrying pipe and the equipment associated therewith is ionized through a physical process called "surface ionization" at the filament surface. These sodium ions are collected at the collector by the potential difference provided between the collector and the filament. The ion current flowing through the collector is measured by the ammeter. Thus, the sodium leak from the sodium carrying pipe is detected. It has been known that the ion current is given by the following equation:

$$I_p = \frac{e \cdot n \cdot S}{1 + \frac{1}{2}\exp\{e(I - \psi)/kT\}} \tag{1}$$

where

- e: a single electric charge (Coulomb)
- I: ionized energy of sodium (eV)
- $\psi$: work function of the filament metal (eV)
- k: Boltzmann's constant
- T: filament temperature (°K)
- n: the number of sodium atoms impinging on a unit area of the filament per unit time (pieces $cm^{-2} \cdot S^{-1}$)
- S: filament surface area ($cm^2$)

The above-mentioned SID involves a limitation of detection due to the effects of dark currents. Dark currents may be classified into three types; the first type of dark current is a leakage current flowing through insulators between electrodes, the second type is an ion current attributed to contamination on the filament surface and to the alkali metals which have been undesirably mixed in the filament material during the manufacturing process, and the third type is a dark current due to radiation.

The first type of dark current or leakage current can be reduced to less than $10^{-12}A$ by increasing the insulation resistance. However, the second type of dark current or ion current cannot substantially be reduced when a metal having a low melting point (e.g. below 2500° C.) is used. In particular, this type of dark current tends to increase with time, and in the case of platinum, a dark current of 1 to 3 nA will increase up to 5 to 20 nA after the filament is exposed to a sodium containing gas for several hours. Thus, the capability of detection is degraded with time. Finally, an increase in the third dark current is also unavoidable unless radioactivity is decreased.

A sensor for detecting sodium leaks by measuring the sodium ion current by means of an ammeter is disclosed, for example, in U.S. Pat. No. 4,117,396.

SUMMARY OF THE INVENTION

It is an object of this invention to provide a sodium ionization detector capable of accurately detecting sodium leaks in which ion current fluctuations are taken into consideration.

It is another object of this invention to provide a sodium ionization detector in which the sodium leak detecting capability will not largely change with time.

It is still another object of this invention to provide a sodium ionization detector having a high detection sensitivity for sodium leaks of low concentration.

It is still another object of this invention to provide a sodium ionization detector in which the sodium leak detection time is relatively short.

It is still another object of this invention to provide an inexpensive sodium ionization detector having an extremely simplified circuit configuration.

The present invention is based on the experimental result that the concentration of sodium in a gas is related to the magnitude of the fluctuation of the ion current. That is, the present invention is characterized in that sodium leaks are detected by measuring the magnitude of the fluctuation of ion current.

BRIEF DESCRIPTION OF THE DRAWINGS

FIGS. 8a to 8c show input and output waveforms at some points in the sodium ionization detector shown in FIG. 7.

FIG. 10 shows an arrangement according to still another embodiment of the present invention.

DESCRIPTION OF THE PREFERRED EMBODIMENTS

Before describing the present invention, the above-mentioned prior art system will be described with reference to the accompanying drawings.

Figure 1:
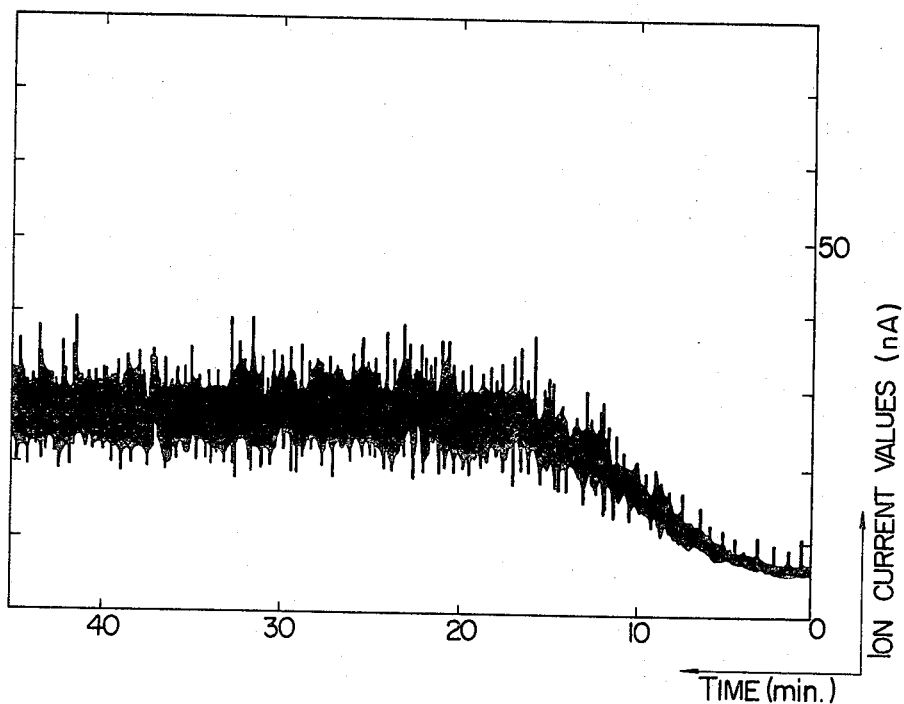
FIG. 1 shows ion current waveforms.

FIG. 1 shows waveforms of an ion current measured by an ammeter. The axis of abscissa corresponds to time (min.) while the axis of ordinate corresponds to ion current value (nA). As can be seen from FIG. 1, the output signal from the SID includes a fluctuation of several Hz called SAS (sodium aerosol spike).

Figure 2:
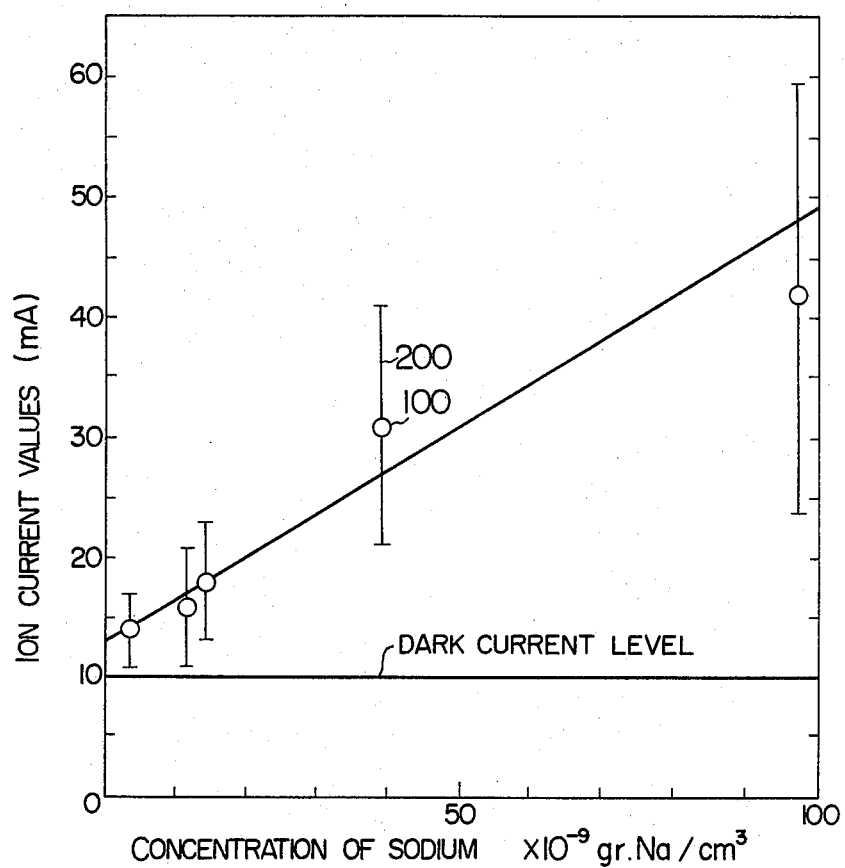
FIG. 2 shows dark currents contained in ion current.

FIG. 2 shows a relationship between the above-described dark current, the output signal of SID, and the concentration of sodium. The axis of abscissa corresponds to the concentration of sodium while the axis of ordinate corresponds to the ion current. The error 200 at each measured point 100 indicates the magnitude of the fluctuation shown in FIG. 1. Assuming that the dark current is 10 mA in FIG. 2, the ratio of the SID output to the dark current only increases from 1.2 to 4 in the range of the concentration of sodium of 1 to $100 \times 10^{-9}$ g/cm$^3$. The output level at the concentration of $100 \times 10^{-9}$ g/cm$^3$ is only about three times as large as that at $1 \times 10^{-9}$ g/cm$^3$, and such a small change or increase is not enough to relate the ion current to the concentration of sodium in a gas. Particularly in case of a low concentration of sodium, sodium leaks can hardly be detected.

Figure 3:
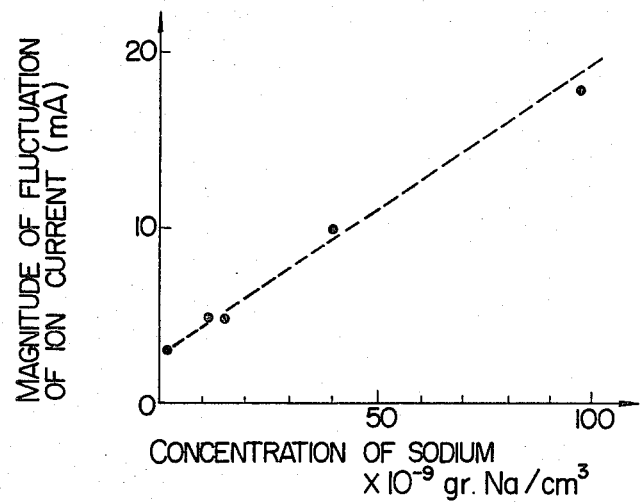
FIG. 3 shows the principle of the present invention.

FIG. 3 shows the magnitude of ion current fluctuation. The axis of ordinate corresponds to the concentration of sodium. As apparent from FIG. 3, the magnitude of ion current fluctuation at the concentration of $100 \times 10^{-9}$ is about six times as large as that at $1 \times 10^{-9}$, and the linearity of the ion current fluctuation characteristic is substantially better than that of the output current characteristic. Therefore, this invention utilizes only the magnitude of fluctuation extracted from the ion current.

Figure 4:
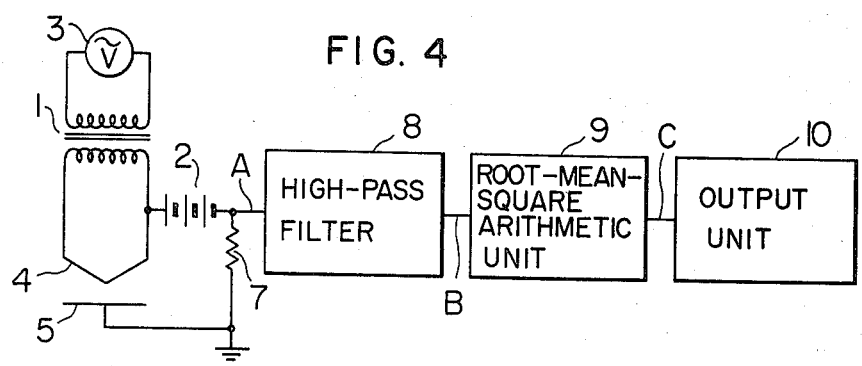
FIG. 4 shows an arrangement according to one embodiment of the present invention.

FIG. 4 shows one embodiment of the present invention. Referring to FIG. 4, a transformer 1 is provided. The transformer 1 includes a primary winding connected to an A.C. high power supply 3, and a secondary winding connected to a filament 4. A collector 5 is also provided, and between the collector 5 and the filament 4, a potential difference is applied by a D.C. power supply 2. A load resistance 7 is connected between the collector 5 and the negative terminal of the D.C. power supply 2. The output end of the load resistance 7 (i.e. the junction between the load resistance and the D.C. power supply) is connected through a high-pass filter 8 to a root-mean-square arithmetic unit 9 (hereinafter abbreviated to RSM arithmetic unit). Output from the RSM unit 9 is supplied to an output unit. The output voltage across the load resistance 7 is applied to the high-pass filter 8 so as to extract fluctuation components only.

The RMS arithmetic unit 9 operates to provide a D.C. output which is the average amplitude value of a fluctuation occurring in a particular period of time T. The arithmetic operation by the RMS arithmetic unit 9 is defined as follows:

$$\Delta E_{RMS} = \sqrt{\frac{1}{T} \int_O^T [\Delta E(t)]^2 dt} \qquad (2)$$

where $\Delta E_{RMS}$: the RMS value of amplitude of fluctuation $\Delta E$: the amplitude of fluctuation.

The D.C. output value produced by the RMS arithmetic unit 9 is compared with predetermined values in the output unit 10, and displayed directly.

Figure 5:
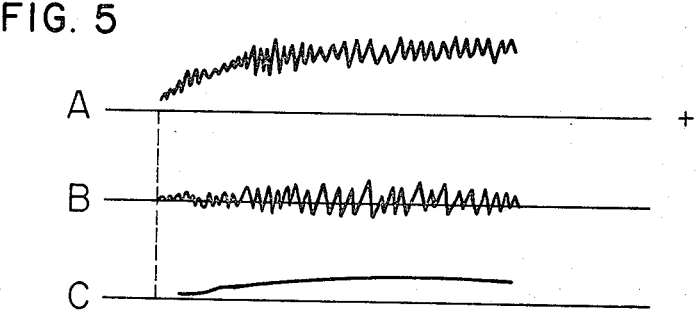
FIG. 5 shows input and output waveforms at some points in the sodium ionization detector shown in FIG. 4.

FIG. 5 shows input and output waveforms at some points in the SID illustrated in FIG. 4. Waveforms A, B and C indicate an input signal to the high-pass filter 8, an output signal from the high-pass filter, and an output signal from the RMS arithmetic unit 9, respectively.

Figure 6:
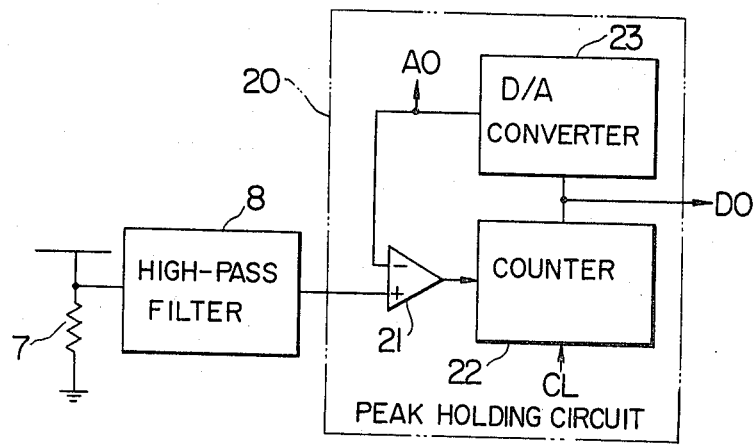
FIG. 6 shows an arrangement according to another embodiment of the present invention.

FIG. 6 shows another embodiment of the present invention. In this embodiment, a peak holding circuit 20 is connected to the output terminal of the high-pass filter 8. The peak holding circuit 20 comprises a comparator 21, a counter 22 for receiving the output signal from the comparator 21 and the clock pulse (CL) from a clock pulse generator (not shown), and a D/A converter 23 connected between the negative input terminal of the comparator 21 and the output terminal of the counter 22.

In operation, only the fluctuation is first extracted by the filter 28 and then supplied to the positive input terminal of the comparator 21. The comparator 21 compares the positive input signal with the negative input signal and produces an output only when the positive input signal is greater than the other. Therefore, when the output from the filter 8 exceeds the output from the D/A converter 23, the comparator 21 produces an output to enable the input gate of the counter 22, thus permitting the clock pulse (CL) to enter the counter 22. As long as the output from the comparator 21 exists, the input gate is kept enabled and the counter 22 counts clock pulses (CL) entering through the gate. The count value of the counter 22 is delivered as a digital output (DO) for external use and also supplied to the D/A converter 23 in which it is converted into an analog signal. The analog signal or analog output (AO) is delivered for external use and also supplied to the negative input terminal of the comparator 21. According to the above-described arrangement, when the output from the filter 8 exceeds the analog output from the D/A converter 23, the counter 22 counts up until its count equals the maximum value of the amplitude. Thus, the maximum value of fluctuation components in the SID can be detected.

The digital output and the analog output values are essentially the same. Use of either the analog output or the digital output depends on whether the associated external processing system is an analog system or a digital system.

In the above-described embodiments, the lower limit of detection of the SID is determined by the extent to which the offset voltage of the circuit can be reduced. Thus, sodium leaks can be detected independent of the effects of dark currents. However, the integration time constant of the RMS arithmetic unit 9 must be made relatively large because the frequency of fluctuation of the ion current is small. This involves the problem that the detection response time of the SID becomes long.

An example of the SID wherein the detection response time is shortened may be provided. In this embodiment, a signal including a fluctuation of the SID and a high frequency reference signal belonging to a different band from that of the SID signal are superposed with each other, and the resultant signal is processed so that its average frequency is obtained. That is, in this embodiment, the averge amplitude of fluctuation of the ion current is converted into an average frequency, and the degree of change in the average frequency is utilized to detect sodium leaks.

Figure 7:
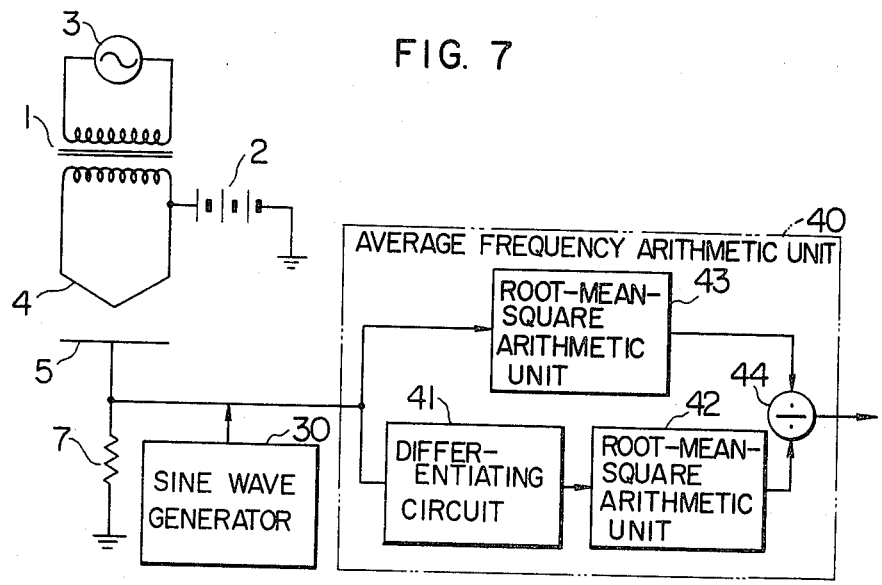
FIG. 7 shows an arrangement according to still another embodiment of the present invention.

Referring to FIG. 7, a sine wave generator 30 is provided. The reference signal derived from the sine wave generator 30 is superposed with the ion current from the collector 5. The superimposed signal is supplied to an average frequency arithmetic unit 40. The average frequency arithmetic unit 40 comprises a differentiating circuit 41, RMS arithmetic units 42 and 43, and a divider 44. The average frequency arithmetic unit 40 produces a D.C. signal which corresponds to the average frequency of the superimposed signal.

In order to generally describe this embodiment, the assumption is made that the input signal V(t) to the average frequency arithmetic circuit 40 is expressed by a Fourier series as follows:

$$V(t) = \Sigma A_j \sin 2\pi f_j t \qquad (3)$$

Then, the average frequency arithmetic unit 40 carries out the following arithmetic operation.

$$\bar{f} = \frac{\sqrt{\sum_j f_j^2 A_j^2}}{\sqrt{\sum_j A_j^2}} = \frac{1}{2\pi}\frac{\sqrt{\dot{V}^2(t)_{RMS}}}{\sqrt{V^2(t)_{RMS}}} \quad (4)$$

where
$f_j$: frequency of the j-th component
$A$: amplitude of the frequency $f_j$
$\bar{f}$: average frequency in the expression (4), the value of the numerator is contained from the RMS arithmetic unit 43 and the value of the denominator is obtained from the differentiating circuit 41 and the RMS arithmetic unit 42. These values are supplied to the divider 44 which, in turn, carries out the arithmetic operation to solve the expression (4).

In the expression (4), the terms marked with RMS means values averaged with time. The values are determined by the integration time constants of the RMS arithmetic units 42 and 43. However, it is not necessary to increase the integration time constant, as distinct from the previously described embodiments, because the input to the average frequency arithmetic unit 40 includes high frequency components.

The input V(t) is a signal produced by superposing the SID output on the output from the sine wave generator 30. If the average frequency of the SID output fluctuation is $f_1$ and the amplitude of fluctuation is $V_1$, then $V_1$ may be expressed nearly by the following expression when the concentration of sodium in the gas is $C_{Na}$.

$$V_1 \approx \alpha C_{Na} \quad (5)$$

where $\alpha$ is a constant. If the frequency of the sine wave generator 30 is $f_2$ and its amplitude is $V_2$, the expression (4) can be rewritten as follows:

$$f_0 = \frac{\sqrt{f_1^2 V_1^2 + f_2^2 V_2^2}}{\sqrt{V_1^2 + V_2^2}} = \frac{\sqrt{f_1^2 \alpha^2 C_{Na}^2 + f_2^2 V_2^2}}{\sqrt{\alpha^2 C_{Na}^2 + V_2^2}} \quad (6)$$

Typical waveforms in this case are shown in FIG. 8a, FIG. 8b and FIG. 8c, in which FIG. 8a, FIG. 8b and FIG. 8c represent in waveform the SID output, the reference wave, and the superposed wave resulted from both waves, respectively. According to the expression (6), if the concentration of sodium $C_{Na}$ in the gas is relatively high, $f_0$ approaches $f_1$, and if the concentration $C_{Na}$ is relatively low, $f_0$ approaches $f_2$. Superposing the reference signal on the SID signal means to insure rapid response of the detector as described previously, and also to maintain the correlation between the detector output and the concentration of sodium. This correlation could not be maintained without the reference signal employed. The signal processing according to this embodiment does not require any high-pass filter, thereby enabling the output offset voltage to be reduced substantially. This improves the detection capability.

The nature of the sinusoidal reference wave, especially the relation of the accuracy of detection to the amplitude $V_2$ and frequency $f_2$ of the reference wave, will be described below.

The expression (6) is rewritten as follows:

$$f_0 = \frac{\sqrt{f_1^2 V_1^2 + f_2^2 V_2^2}}{\sqrt{V_1^2 + V_2^2}} = \frac{\sqrt{f_1^2 (V_1/V_2)^2 + f_2^2}}{\sqrt{(V_1/V_2)^2 + 1}} \quad (7)$$

$$= \frac{\sqrt{f_1^2 k^2 + f_2^2}}{\sqrt{k^2 + 1}}$$

where k is a ratio of the signal voltage $V_1$ derived from sodium aerosol to the signal voltage $V_2$ of the reference wave. Because $V_1 = \alpha C_{Na}$, k increases with the increase in the concentration of sodium and with the decrease in the reference wave amplitude $V_1$. The signal derived from sodium aerosol has a frequency range of several Hz. When $f_1$ is represented by a value of 0.5 Hz, $f_0$ for various values of $f_2$ is calculated with k as parameter and shown in FIG. 9.

Figure 9:
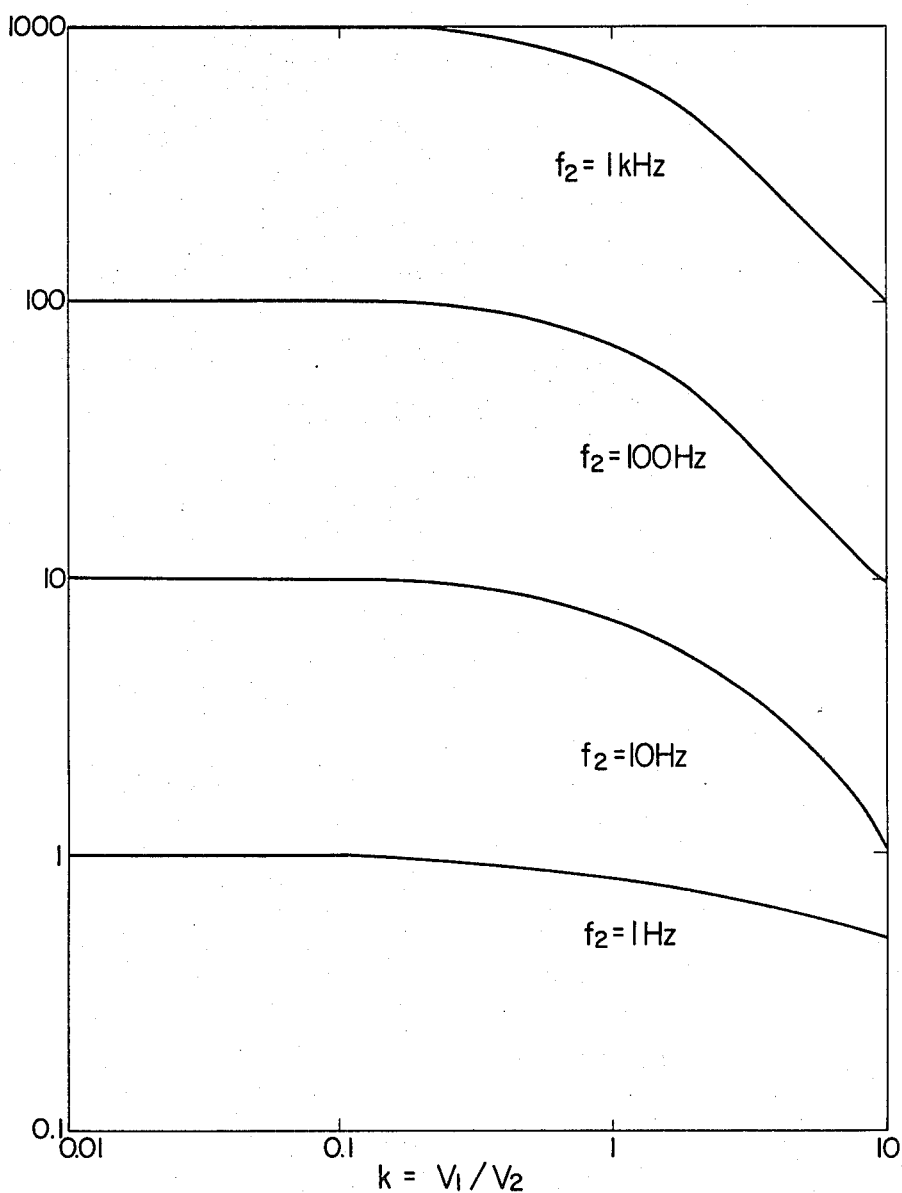
FIG. 9 shows a graphical representation illustrating the operation of the sodium ionization detector shown in FIG. 7.

Referring to FIG. 9, it can be seen, for example, that when the reference wave frequency $f_2$ is 1 Hz, $f_0$ varies so little with the change in the k value that the correlation between $f_0$ and the concentration of sodium is not sufficient. When $f_2$ is 10 Hz or higher, the $f_0$ curves have substantially the same gradient within a range of the k value of 1 to 10, and their correlations with the concentration of sodium are substantially the same. With $f_2 = 1$ Hz or higher, only little change in the $f_0$ value can be appreciated if k is less than about 0.3, and therefore k should be more than 0.3. This indicates that sufficient changes in the $f_0$ value will not appear unless the reference wave amplitude $V_2$ is greater than at least one-third of the amplitude of the signal derived from sodium aerosol. Since $V_1$ can be varied properly by an amplifier, there is no use in specifying a particular value for $V_2$. A proper range of the reference wave frequency may be higher than 10 Hz.

FIG. 10 shows another embodiment of the present invention in which reference numerals 9 and 30 designate a RMS arithmetic unit and a sine wave generator, and a frequency-voltage converter 36 is provided in place of the average frequency arithmetic unit 40 shown in FIG. 7. In this embodiment, the output does not represent an average frequency in the strict sense. However, since a deviation from the output voltage according to the reference wave frequency occurs in accordance with the amount of sodium contained in the gas, this embodiment also presents the same effect as the embodiment shown in FIG. 7.

It should be noted that besides the RMS operation there may be various methods for extracting fluctuation components alone. For example, a sampling process may be useful. In such a case, the sampling period should be shorter than the period of fluctuation components.

As described above, the present invention serves to improve the accuracy of detection by eliminating errors involved in the conventional detecting process for dark currents.

We claim:
1. A sodium ionization detector comprising thermal ionizer means for thermally ionizing sodium to produce an ion current, and detector means for detecting the magnitude of fluctuation of said ion current by detecting the RMS value of the amplitude of a sodium aerosol spike component of said ion current.

2. A sodium ionization detector comprising:

surface ionizer means for ionizing sodium to produce an ion current; and detector means for detecting the magnitude of a sodium aerosol spike of said ion current, said detector means including filter means for extracting the sodium aerosol spike component from said ion current, and arithmetic means for calculating the RMS value of amplitude of the sodium aerosol spike component.

3. A sodium ionization detector as claimed in claim 2, wherein said RMS value of amplitude of sodium aerosol spike is represented by $$\Delta E_{RMS} = \sqrt{\frac{1}{T} \int_O^T [\Delta E(t)]^2 dt} \ .$$

* * * * *